(12) United States Patent
Kurian et al.

(10) Patent No.: US 11,311,315 B2
(45) Date of Patent: Apr. 26, 2022

(54) MULTI-PLATE CAPACITIVE ASSEMBLY FOR A SPINAL IMPLANT

(71) Applicant: Warsaw Orthopedic, Inc., Warsaw, IN (US)

(72) Inventors: Arjun S. Kurian, Memphis, TN (US); Nicholas Benson, Collierville, TN (US); Newton Metcalf, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 198 days.

(21) Appl. No.: 16/733,577

(22) Filed: Jan. 3, 2020

(65) Prior Publication Data

US 2021/0204983 A1 Jul. 8, 2021

(51) Int. Cl.
*A61B 17/70* (2006.01)
*A61B 17/86* (2006.01)
(Continued)

(52) U.S. Cl.
CPC ...... *A61B 17/7032* (2013.01); *A61B 17/8685* (2013.01); *G01D 5/24* (2013.01);
(Continued)

(58) Field of Classification Search
CPC . A61B 17/7032; A61B 17/8685; A61B 17/84; A61B 17/8605; A61B 2017/0003; A61B 2017/00526; A61B 2017/00867; A61B 2017/0088; A61B 2017/00933; A61B 2017/00955; G01D 5/24; H01G 4/01; H01G 4/40
(Continued)

(56) References Cited

U.S. PATENT DOCUMENTS 5,683,432 A 11/1997 Goedeke et al.
6,004,349 A 12/1999 Jackson
(Continued)

FOREIGN PATENT DOCUMENTS

WO 2015200720 A2 12/2015

OTHER PUBLICATIONS

International Search Report, PCT/US2019/042516, dated Oct. 31, 2019.
(Continued)

*Primary Examiner* — Ellen C Hammond
*Assistant Examiner* — David C Comstock
(74) *Attorney, Agent, or Firm* — Fox Rothschild LLP (57) ABSTRACT

A spinal implant assembly includes a set screw having a central opening that extends from a first end of the set screw toward a second end of the set screw. The second end of the set screw includes a bottom bore portion, and the set screw is configured to engage with an anchoring member. The spinal implant assembly includes a capacitive assembly having an integrated circuit located within an internal portion the capacitive assembly, and a plurality of capacitive plates positioned on an outside bottom surface of the capacitive assembly. Each of the capacitive plates is in operable communication with the integrated circuit, and the capacitive assembly is configured to be received within the central opening of the set screw, such that the plurality of capacitive plates are positioned above the bottom bore portion.

20 Claims, 5 Drawing Sheets

(51) Int. Cl.
*H01G 4/40* (2006.01)
*H01G 4/01* (2006.01)
*G01D 5/24* (2006.01)
*A61B 17/00* (2006.01)

(52) U.S. Cl.
CPC ............... *H01G 4/01* (2013.01); *H01G 4/40* (2013.01); *A61B 2017/0003* (2013.01); *A61B 2017/0088* (2013.01); *A61B 2017/00526* (2013.01); *A61B 2017/00867* (2013.01); *A61B 2017/00933* (2013.01); *A61B 2017/00955* (2013.01)

(58) Field of Classification Search
USPC ............... 606/266, 267, 270, 305, 308, 328; 73/761, 780, 862.337
See application file for complete search history.

(56) References Cited

U.S. PATENT DOCUMENTS

| | | | |
|---|---|---|---|
| 6,280,445 B1 | 8/2001 | Morrison et al. | |
| 6,378,381 B1* | 4/2002 | Okada | G01D 5/24 73/514.32 |
| 6,485,491 B1 | 11/2002 | Farris et al. | |
| 7,694,590 B2* | 4/2010 | Stratmann | G01G 7/06 73/862.626 |
| 7,698,952 B2* | 4/2010 | Renken | G01L 9/0073 73/780 |
| 7,705,612 B2* | 4/2010 | Morimoto | G01L 5/165 324/661 |
| 8,057,519 B2 | 11/2011 | Justis et al. | |
| 8,584,957 B2* | 11/2013 | Zhu | F16B 31/02 235/492 |
| 2005/0267477 A1 | 12/2005 | Jackson | |
| 2006/0235488 A1* | 10/2006 | Nycz | A61B 90/90 607/60 |
| 2009/0038401 A1* | 2/2009 | Kibblewhite | B60N 2/3095 73/761 |
| 2009/0234391 A1 | 9/2009 | Butler et al. | |
| 2010/0201118 A1 | 8/2010 | Anton et al. | |
| 2015/0292996 A1* | 10/2015 | Hsieh | G01L 5/162 73/761 |
| 2020/0022739 A1* | 1/2020 | Benson | A61B 5/6878 |
| 2020/0022772 A1* | 1/2020 | Benson | A61B 17/7037 |
| 2020/0222092 A1* | 7/2020 | Murali | A61B 34/20 |

OTHER PUBLICATIONS

International Search Report, PCT/US2019/042511, dated Oct. 31, 2019.

* cited by examiner

MULTI-PLATE CAPACITIVE ASSEMBLY FOR A SPINAL IMPLANT

TECHNICAL FIELD

The present disclosure generally relates to capacitive sensor assemblies for implant devices, and more particularly to capacitive sensor assemblies for implant devices that are used to monitor the state or health of the implant devices.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members to assist with the treatment of a spinal disorder. Longitudinal members may provide a stable, rigid column that helps bones to fuse, and may redirect stresses over a wider area away from a damaged or defective region. Also, rigid longitudinal members may help in spinal alignment.

Screw assemblies may be used to connect a longitudinal member to a vertebral member. A screw assembly may include a pedicle screw, hook, or other connector and/or a set screw, among other components. A pedicle screw can be placed in, above and/or below vertebral members that were fused, and a longitudinal member can be used to connect the pedicle screws which inhibits or controls movement. A set screw can be used to secure the connection of a longitudinal member and a pedicle screw, hook or other connector. However, the connection force and continued integrity of the connection between a longitudinal member and a pedicle screw or other connector can be challenging to monitor during and after implantation. In addition, it is difficult to monitor that a proper or acceptable or any force is maintained between a set screw and a longitudinal member.

SUMMARY

In an embodiment, a spinal implant assembly includes a set screw having a central opening that extends from a first end of the set screw toward a second end of the set screw. The second end of the set screw includes a bottom bore portion, and the set screw is configured to engage with an anchoring member. The spinal implant assembly includes a capacitive assembly having an integrated circuit located within an internal portion the capacitive assembly, and a plurality of capacitive plates positioned on an outside bottom surface of the capacitive assembly. Each of the capacitive plates is in operable communication with the integrated circuit, and the capacitive assembly is configured to be received within the central opening of the set screw, such that the plurality of capacitive plates are positioned above the bottom bore portion.

Each quadrant of the outside bottom surface of the capacitive assembly may include at least one of the capacitive plate.

Each capacitive plate and the bottom bore portion may form a capacitor.

One or more of the capacitive plates may include a plurality of response zones, each having an electrical conductor, and one or more gaps between the plurality of response zones. The plurality of response zones may include a central round response zone, and a plurality of curved response zones surrounding the central round response zone.

The integrated circuit may include memory. The integrated circuit may be configured to store one or more measurements made by the capacitive assembly in the memory, and transmit the one or more measurements to a reader when the reader is in proximity to the integrated circuit.

The integrated circuit may include memory, and the integrated circuit may be configured to store a unique identifier associated with the set screw in the memory; and transmit the unique identifier to a reader when the reader is in proximity to the integrated circuit.

The integrated circuit may include one or more of the following: a radio frequency identification (RFID) chip, or a near-field communication (NFC) chip.

Optionally, a gap may exist between each of the capacitive plates and the bottom bore portion.

In an embodiment, a spinal implant assembly includes a set screw having a central opening that extends from a first end of the set screw toward a bottom bore portion of the set screw, and a capacitive assembly having a plurality of capacitive plates positioned on an outside bottom surface of the capacitive assembly. The capacitive assembly is configured to be received within the central opening of the set screw such that the plurality of capacitive plates are positioned above the bottom bore portion.

Each quadrant of the outside bottom surface of the capacitive assembly may include at least one of the capacitive plate.

Each plate and the bottom bore portion may form a capacitor.

One or more of the capacitive plates may include a plurality of response zones, each having an electrical conductor, and one or more gaps between the plurality of response zones. The plurality of response zones may include a central round response zone, and a plurality of curved response zones surrounding the central round response zone.

The capacitive assembly may further include an integrated circuit having memory. The integrated circuit may be configured to store one or more measurements made by the capacitive assembly in the memory, and transmit the one or more measurements to a reader when the reader is in proximity to the integrated circuit.

The capacitive assembly may further include an integrated circuit having memory. The integrated circuit may be configured to store a unique identifier associated with the set screw in the memory, and transmit the unique identifier to a reader when the reader is in proximity to the integrated circuit.

The capacitive assembly may further include an integrated circuit having one or more of the following: a radio frequency identification (RFID) chip, or a near-field communication (NFC) chip.

A gap may exist between each of the capacitive plates and the bottom bore portion.

DETAILED DESCRIPTION

The exemplary embodiments of the surgical system and related methods of use disclosed are discussed in terms of medical devices for the treatment of musculoskeletal disorders and more particularly, in terms of vertebral fixation screws, including for example pedicle screws, as well as hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of load sensing systems include, for example, U.S. Pat. Nos. 6,485,491 and 8,057,519, all incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral pedicle screw system and related components and methods of employing the vertebral pedicle screw in accordance with the principles of the present disclosure. Reference is made in detail to the exemplary embodiments of the present disclosure, which are illustrated in the accompanying figures.

The components of the vertebral pedicle screw system described herein can be fabricated from biologically acceptable materials suitable for medical applications, including metals, synthetic polymers, ceramics and bone material and/or their composites. For example, the components of the vertebral pedicle screw system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral pedicle screw system may be formed of constructed material composites, including the above materials, to achieve various desired characteristics such as strength, rigidity, elasticity, compliance, biomechanical performance, durability and radiolucency or imaging preference. The components of the present vertebral pedicle screw system, individually or collectively, may also be fabricated from a heterogeneous material such as a combination of two or more of the above-described materials. The components of the vertebral pedicle screw system may be monolithically formed, integrally connected or include fastening elements and/or instruments, as described herein. The components of the vertebral pedicle screw system may be formed using a variety of subtractive and additive manufacturing techniques, including, but not limited to machining, milling, extruding, molding, 3D-printing, sintering, coating, vapor deposition, and laser/beam melting. Furthermore, various components of the vertebral pedicle screw system may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral pedicle screw system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral pedicle screw system may be employed with surgical procedures, as described herein, and/or, for example, corpectomy, discectomy, fusion and/or fixation treatments that employ spinal implants to restore the mechanical support function of vertebrae. In some embodiments, the pedicle screw system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example). In some embodiments, an implant may be employed for the treatment of spinal disease and/or deformity conditions including, without limitation, scoliosis, spondylolisthesis, and/or the like.

Figure 1:
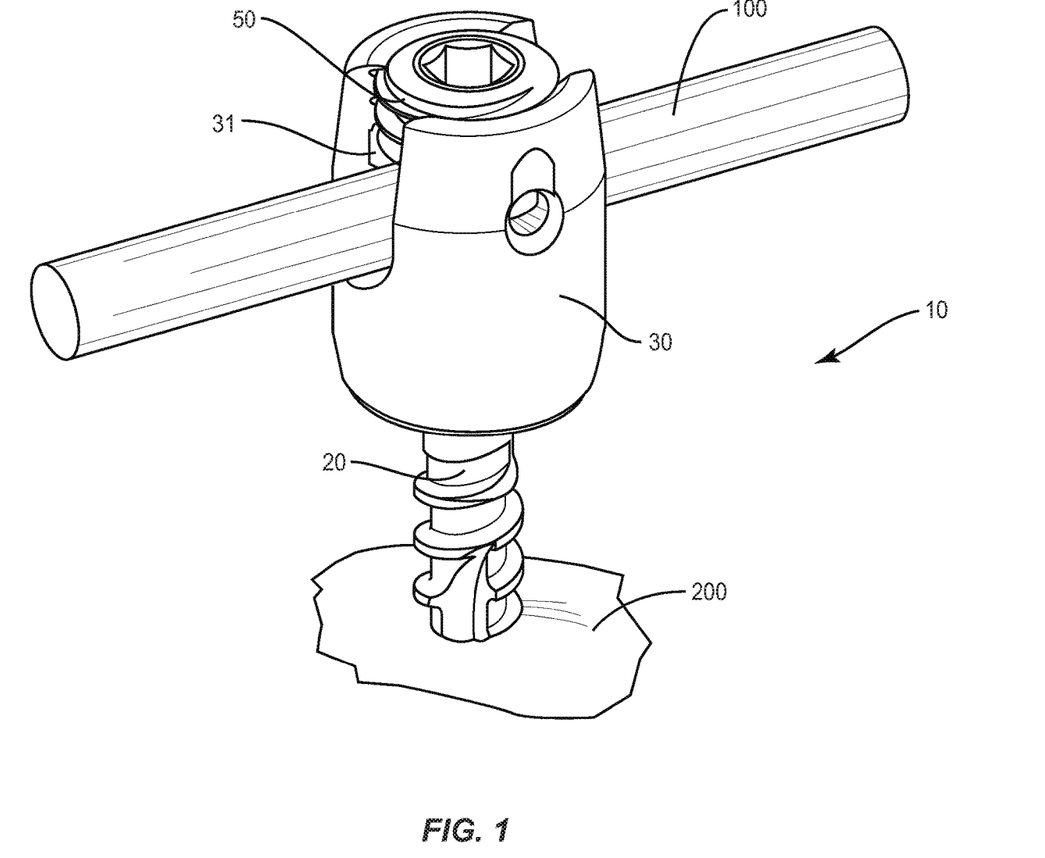
FIG. 1 illustrates an example anchoring assembly and longitudinal member according to an embodiment.

FIG. 1 illustrates an example anchoring assembly and longitudinal member according to an embodiment. As illustrated in FIG. 1, an anchoring assembly includes a screw 20 and an anchoring member 30. The screw 20 has an elongated shape with a first end mounted within a vertebral member 200 and a second end extending outward above the vertebral member 200. The anchoring member 30 is configured to operatively connect to the second end of the screw 20 and is movably connected to the screw 20 to accommodate the longitudinal member 100 positioned at various angular positions. The anchoring member 30 includes a channel 31 sized to receive the longitudinal member 100. A set screw 50 attaches to the anchoring member 30 to capture the longitudinal member 100 within the channel 31.

Figure 2:
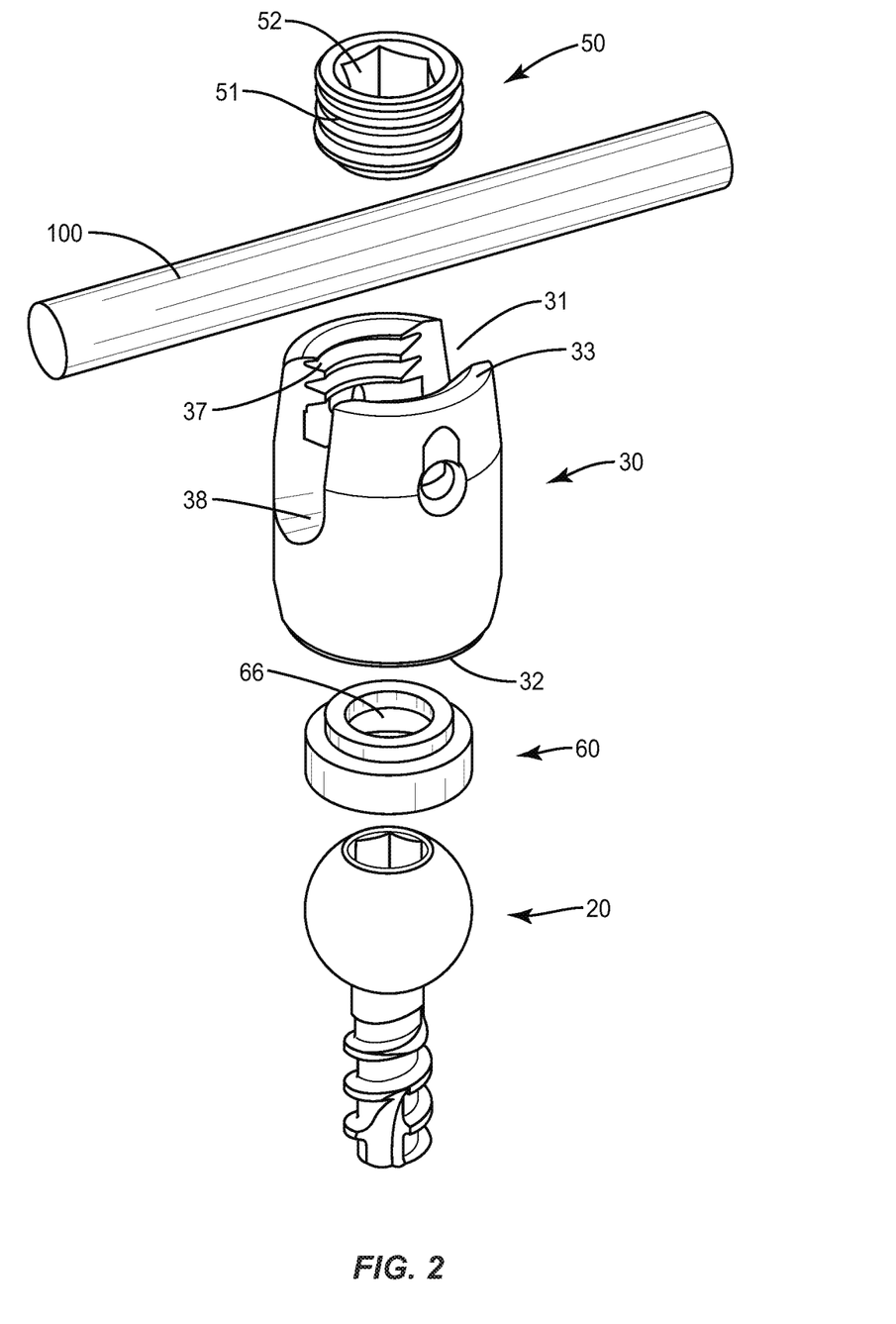
FIG. 2 illustrates an example exploded view of a screw assembly and longitudinal member according to an embodiment.

FIG. 2 illustrates an example exploded view of a screw assembly and longitudinal member according to an embodiment. As shown by FIG. 2, anchoring member 30 provides a connection between the screw 20 and longitudinal member 100. Anchoring member 30 includes a first end 32 that faces towards the vertebral member 200, and a second end 33 that faces away. A chamber is positioned between the first and second ends 32, 33 and is sized to receive at least a portion of the screw 20. In various embodiments, a first end 32 may be considered a base portion of an anchoring member 30, and a second end 33 may be considered a head portion of an anchoring member.

The second end 33 of the anchoring member 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the anchoring member 30 facing towards the channel 31. In another embodiment, the threads 37 may be on the exterior of the anchoring member 30. An interior of the anchoring member 30 may be open between the first and second ends 32, 33.

In various embodiments, an anchoring member 30 may include a washer 60. A washer 60 may be generally cylindrical and may have a hole 66 therethrough. As illustrated by FIG. 1 a washer 60 may be positioned near a first end 32 of an anchoring member 30. A screw 20 may engage with an anchoring member 30 via positioning through the hole 66 of a washer 60. A washer 60 may include recessed portions which may be configured to accommodate placement of a longitudinal member 100 therein. The use of a washer 60 in connection with an anchoring member 30 may help minimize misalignment of the longitudinal member within the anchoring member.

In an embodiment, set screw 50 attaches to the anchoring member 30 and captures the longitudinal member 100 within the channel 31. As illustrated in FIG. 2, the set screw 50 may be sized to fit within the interior of the channel 31 and include exterior threads 51 that engage threads 37 on the anchoring member 30. A driving feature 52 may be positioned on a top side to receive a tool during engagement with the anchoring member 30. In some embodiments, the set screw 50 may be mounted on an exterior of the anchoring member 30. Set screw 50 includes a central opening and is sized to extend around the second end 33. A set screw 50 may be a break-off set screw or a non-break-off set screw. In certain embodiments, a set screw 50 may include a slot 53 for receiving or routing of electronic connections as illustrated in FIGS. 13A and 13B. Threads 51 are positioned on an inner surface of the central opening to engage with the external threads 37 on the anchoring member 30. The set screw 50 and anchoring member 30 may be constructed for the top side of the set screw 50 to be flush with or recessed within the second end 33 when mounted with the anchoring member 30.

Figure 3:
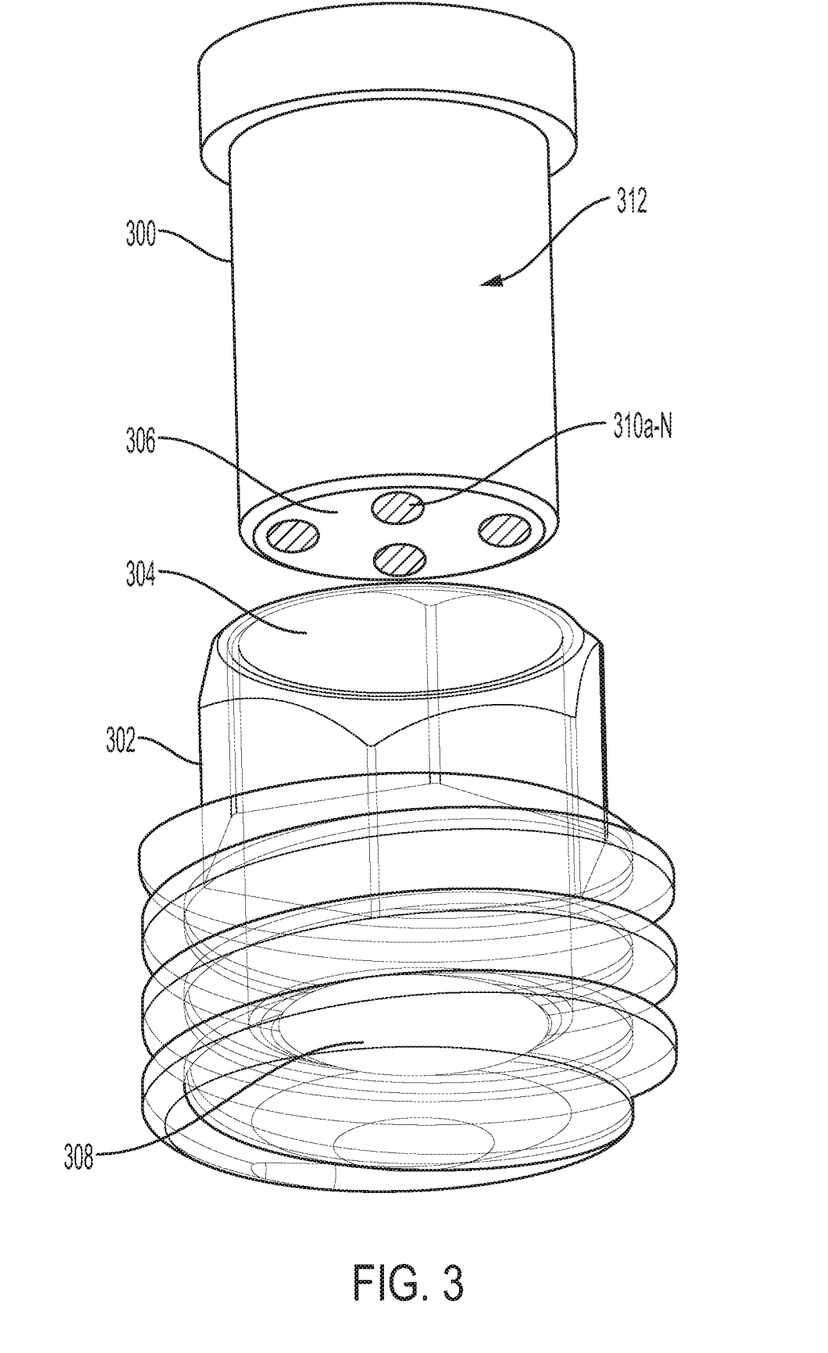
FIG. 3 illustrates an example capacitive assembly for a set screw according to an embodiment.

FIG. 3 illustrates an example capacitive assembly for an example set screw according to an embodiment. As illustrated by FIG. 3, a capacitive assembly 300 may be shaped and/or sized to be at least partially received by an opening 304 of a set screw 302. For instance, FIG. 3 illustrates a set screw 302 having a generally cylindrical opening and a capacitive assembly 300 also having a generally cylindrical shape. Additional and/or alternate shapes may be used within the scope of this disclosure.

A capacitive assembly 300 may have one or more internal components. The internal components may include one or more electronic components. In various embodiments, one or more electronic components may facilitate communication between the capacitive assembly 300 and one or more other devices and/or assemblies. Such devices and/or assemblies may be part of the same implant, or they may be part of another implant or device, either within or external to a patient.

In various embodiments, an electronic component that may be part of a capacitive assembly may be antenna, such as a radio frequency identification (RFID) coil, a near field-communication (NFC) antenna or other short-range communication transmitter and/or receiver. A capacitive assembly may include one or more integrated circuits such as, for example, an RFID chip or an NFC chip. In another embodiment, an integrated circuit may include a custom radio frequency communication scheme or protocol. In an embodiment, one or more of the electronic components may include a flexible electronics component, such as, for example, a flex circuit or one or more electrical circuits. An integrated circuit may include memory according to an embodiment. The memory may be used to store various information. For example, one or more measurements of a capacitive assembly may be stored in memory. As another example, a unique identifier associated with a capacitive assembly, a component thereof, or a set screw may be stored in memory. Additional and/or alternate information or types of information may be stored according to this disclosure.

In various embodiments, an integrated circuit may be located within at least a portion of a capacitive assembly 300. For example, FIG. 3 illustrates a capacitive assembly having an exterior and an internal portion 312. The one or more integrated circuits or other electrical components may be located within the internal portion 312.

As illustrated in FIG. 3, a bottom surface 306 of a capacitive assembly 300 may be received by an opening 304 of a set screw 302 such that at least a portion of the bottom surface is positioned in proximity to a bottom bore 308 of the set screw. In various embodiments, the bottom surface 306 of the capacitive assembly may include one or more capacitive plates 310a-N. Each capacitive plate 310a-N may be strategically placed along the bottom surface of the capacitive assembly to increase sensitivity and specificity of measurements of the strain and surface topography of the bottom bore 308. For instance, a capacitive plate 310a-N may be located in each quadrant of the bottom surface of the capacitive assembly 300. These measurements may provide valuable information pertaining to the integrity of the construct and fusion status of an implant. In various embodiments, one or more of the capacitive plates 310a-N may be in operable communication with an integrated circuit or other electrical components of a capacitive assembly 300.

Figure 4:
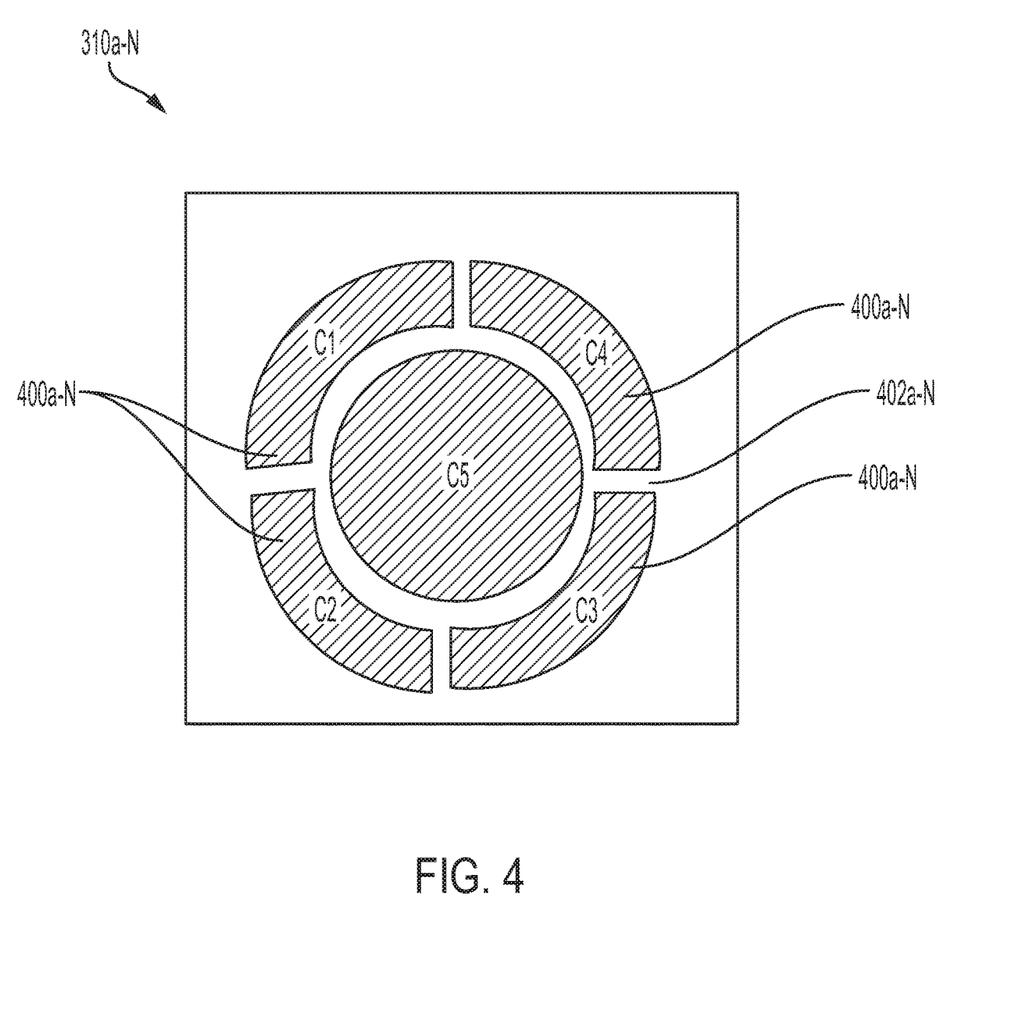
FIG. 4 illustrates an example capacitive plate according to an embodiment.

FIG. 4 illustrates an example capacitive plate 310a-N according to an embodiment. As illustrated in FIG. 4, a capacitive plate 310a-N may include one or more response zones 400a-N. A capacitive plate 310a-N may include one or more response zones separated by one or more gaps 402a-N. A response zone refers to a portion of a capacitive plate having an electrical conductor, such as, for example, a metal portion. A gap 402a-N refers to a portion not having an electrical conductor.

As illustrated in FIG. 4, a capacitive plate 310a-N may have five response zones 400a-N with gaps 402a-N between at least a portion of the response zones. One response zone may be centrally located and may have a generally circular shape. The other response zones may have a generally curved shape and may be positioned around the outside of the centrally positioned response zone. It is understood that differently shaped and/or positioned response zones may be used within the scope of this disclosure. It is also understood that additional and/or fewer response zones may be used within the scope of this disclosure.

In various embodiments, one or more of the capacitive plates 310a-N and the bottom bore 308 of a set screw may form a capacitor. For instance, when the capacitive assembly 300 is positioned within a central opening 304 of a set screw 302 the capacitive plates may be positioned above the bottom bore 308 of the set screw. The air between the capacitive plates 310a-N and the bottom bore 308 may act as a dielectric medium.

Figure 5:
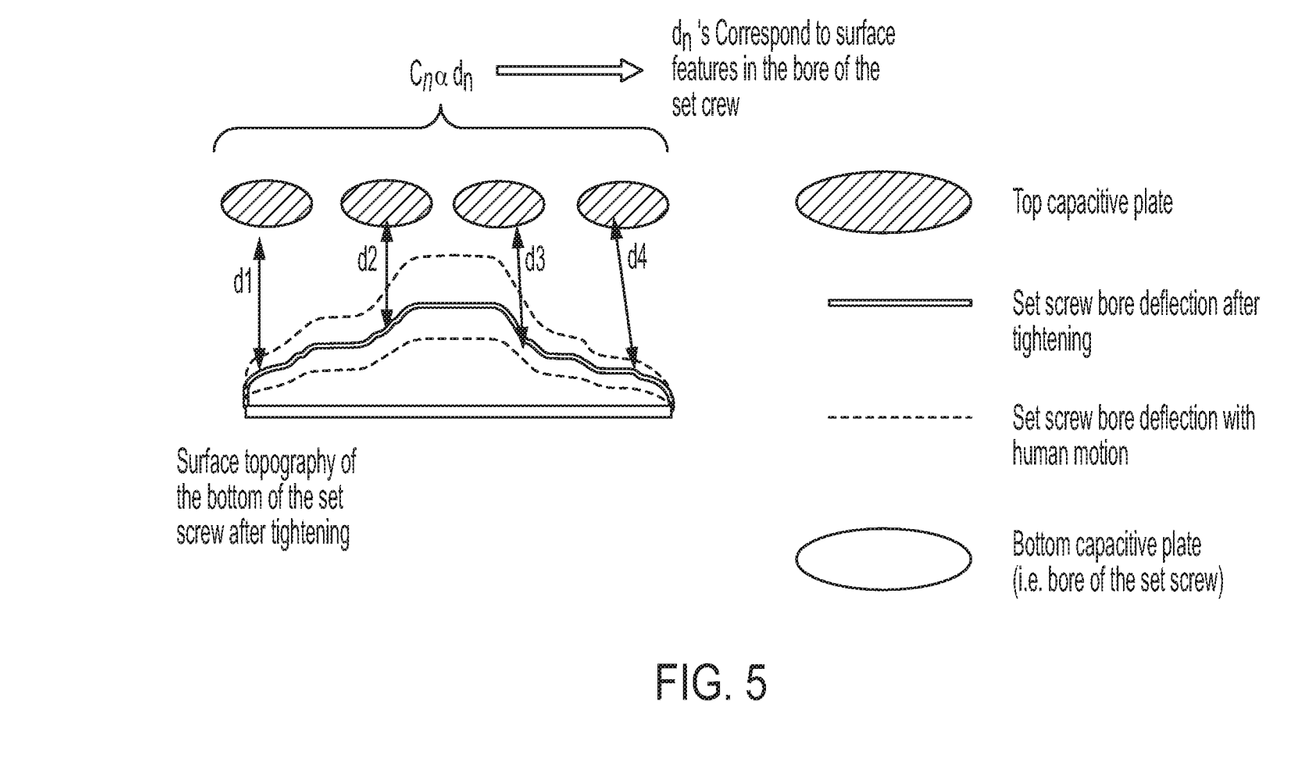
FIG. 5 illustrates an example hook member according to an embodiment.

FIG. 5 illustrates a diagram showing an example correlation of the surface topography of the bottom bore 308 of a set screw to capacitive plates 310a-N according to an embodiment.

In various embodiments, the capacitance measured between one or more of the capacitive plates 310a-N and the bottom bore may indicate a measure of the construct integrity and/or fusion status of an implant.

FIGS. 1-4 illustrate a multi-axial tulip-head pedicle screw according to various embodiments. However, it is understood that other types of anchoring members may be used within the scope of this disclosure. For example, fixed head screws or screws having differently shaped heads may be used. As another example, a hook member, a cross-link connector, an offset connector, or a hybrid hook-screw member may be used as well. FIG. 5 illustrates an example hook member according to an embodiment.

In various embodiments, one or more measurements obtained by a capacitive assembly may be stored by an integrated circuit of a corresponding capacitive assembly such as, for example, in its memory. The integrated circuit may be interrogated by a reader. For instance, an RFID chip may be read by an RFID reader. As another example, an NFC chip may be read by or may otherwise communicate with an NFC reader or other NFC-enabled device. A reader may interrogate an integrated circuit when in a certain proximity to the integrated circuit. In certain embodiments, a reader may interrogate an integrated circuit that has been implanted into a patient as part of a set screw or anchoring member assembly. In other embodiments, an integrated circuit may communicate with a reader or other electronic device without being interrogated.

An integrated circuit may transmit one or more measurements to the reader. This transmission may occur in response to being interrogated by the reader, or the transmission may be initiated by the integrated circuit. The reader may receive the transmitted measurements, and may cause at least a portion of the measurements to be displayed to a user. For instance, a physician may use a reader to interrogate an RFID chip of a patient's implant. The reader may include a display, or may be in communication with a display device, which may display at least a portion of the measurements received from the RFID chip.

An integrated circuit may be passive, meaning that the chip has no internal power source and is powered by the energy transmitted from a reader. With respect to an assembly having a passive integrated circuit, the integrated circuit may not transmit information until interrogated by a reader.

In another embodiment, an integrated circuit may be active, meaning that the chip is battery-powered and capable of broadcasting its own signal. An active integrated circuit may transmit information in response to be interrogated by a reader, but also on its own without being interrogated. For instance, an active integrated circuit may broadcast a signal that contains certain information such as, for example, one or more measurements gathered by an associated strain gauge. An active integrated circuit may continuously broadcast a signal, or it may periodically broadcast a signal. Power may come from any number of sources, including, for example, thin film batteries with or without encapsulation or piezo electronics.

In various embodiments, one or more sensors of a capacitive assembly may transmit information by directly modulating a reflected signal, such as an RF signal. The strain gauge sensors may form a Wireless Passive Sensor Network (WPSN), which may utilize modulated backscattering (MB) as a communication technique. External power sources, such as, for example, an RF reader or other reader, may supply a WPSN with energy. The sensor(s) of the WPSN may transmit data by modulating the incident signal from a power source by switching its antenna impedance.

One or more measurements received from a capacitive assembly may be used to make determinations of the condition of a spinal implant and/or provide insights into potential interventions that may inform, improve, or change the treatment course for a spinal condition. For instance, proper placement of a longitudinal member, set screw and/or anchoring member may result in an acceptable range of capacitive measurements collected by a capacitive assembly. Measurements outside of this range may indicate a problem with the placement or positioning of a longitudinal member, set screw and/or anchoring member such as, for example, loosening of a set screw and/or anchoring member, longitudinal member failure, construct failure, yield or fracture/ breakage, improper torque, breakage of the bone segment or portion, the occurrence of fusion or amount of fusion, and/or the like.

One or more tools or instruments may include a reader which may be used to gather information from one or more integrated circuits during or in connection with a procedure. For instance, a torque tool may be used to loosen or tighten a set screw. A torque tool may include a reader, or may be in communication with a reader, such that a user of the torque tool is able to obtain, in substantially real time, one or more measurements relating to the set screw and longitudinal rod placement that are measured by a capacitive assembly of the set screw via the tool. For instance, as a user is applying torque to a set screw, the user may see one or more force measurements between the set screw and the longitudinal member in order to determine that the positioning of the set screw and/or longitudinal member is correct. In certain embodiments, a tool or instrument may include a display device on which one or more measurements may be displayed. In other embodiments, a tool or instrument may be in communication with a display device, and may transmit one or more measurements for display on the display device via a communications network.

In some embodiments, an electronic device, such as a reader or an electronic device in communication with a reader, may compare one or more measurements obtained from an integrated circuit to one or more acceptable value ranges. If one or more of the measurements are outside of an applicable value range, the electronic device may cause a notification to be made. For instance, an electronic device may generate an alert for a user, and cause the alert to be displayed to the user via a display device. Alternatively, an electronic device may send an alert to a user such as via an email message, a text message or otherwise.

An integrated circuit of a load sensing assembly may store a unique identifier associated with the component to which the capacitive assembly corresponds. For instance, an integrated circuit of a load sensing assembly for a set screw may store a unique identifier associated with the set screw. Similarly, an integrated circuit of a capacitive assembly for an anchoring member may store a unique identifier associated with the anchoring member. The integrated circuit may transmit the unique identifier to an electronic device. For instance, when a reader interrogates an integrated circuit, the integrated circuit may transmit a unique identifier for a component that is stored by the integrated circuit to the reader.

Having access to a unique identifier for a component may help a user ascertain whether the measurements that are being obtained are associated with the component of interest. Also, having access to a unique identifier for a component may help a user take inventory of one or more components. For instance, after spinal surgery, a physician or other health care professional may use a reader to confirm that all of the set screws and anchoring members allocated for the procedure have been used and are positioned in a patient.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A spinal implant assembly comprising:
a pedicle screw;
a set screw comprising a central opening that extends from a first end of the set screw toward a second end of the set screw, wherein the second end of the set screw comprises a bottom bore portion, wherein the set screw is configured to engage with an anchoring member, the anchoring member operatively connected to the pedicle screw; and
a capacitive assembly comprising:
an integrated circuit located within an internal portion of the capacitive assembly, and
a plurality of capacitive plates positioned on an outside bottom surface of the capacitive assembly, wherein each of the capacitive plates is in operable communication with the integrated circuit, wherein the capacitive assembly is configured to be received within the central opening of the set screw, such that the plurality of capacitive plates are positioned above the bottom bore portion.

2. The spinal implant assembly of claim 1, wherein the outside bottom surface comprises a substantially circular surface having four quadrants, wherein each quadrant of the outside bottom surface of the capacitive assembly comprises at least one of the capacitive plates.

3. The spinal implant assembly of claim 1, wherein each capacitive plate and the bottom bore portion forms a capacitor.

4. The spinal implant assembly of claim 1, wherein one or more of the capacitive plates comprises:
a plurality of response zones, each comprising an electrical conductor; and
one or more gaps between the plurality of response zones.

5. The spinal implant assembly of claim 4, wherein the plurality of response zones comprise:
a central round response zone; and
a plurality of curved response zones surrounding the central round response zone.

6. The spinal implant assembly of claim 1, wherein the integrated circuit comprises memory, wherein the integrated circuit is configured to:
store one or more measurements made by the capacitive assembly in the memory; and
transmit the one or more measurements to a reader when the reader is in proximity to the integrated circuit.

7. The spinal implant assembly of claim 1, wherein the integrated circuit comprises memory, wherein the integrated circuit is configured to:
store a unique identifier associated with the set screw in the memory; and
transmit the unique identifier to a reader when the reader is in proximity to the integrated circuit.

8. The spinal implant assembly of claim 1, wherein the integrated circuit comprises one or more of the following:
a radio frequency identification (RFID) chip; or
a near-field communication (NFC) chip.

9. The spinal implant assembly of claim 1, wherein a gap exists between each of the capacitive plates and the bottom bore portion.

10. An assembly comprising:
a set screw comprising a central opening that extends from a first end of the set screw toward a bottom bore portion of the set screw; and
a capacitive assembly comprising:
a plurality of capacitive plates positioned on an outside bottom surface of the capacitive assembly, wherein the capacitive assembly is configured to be received within the central opening of the set screw such that the plurality of capacitive plates are positioned above the bottom bore portion, wherein one or more of the capacitive plates comprises:
a plurality of response zones, each comprising an electrical conductor; and one or more gaps between the plurality of response zones, wherein the plurality of response zones comprise:
a central round response zone; and
a plurality of curved response zones surrounding the central round response zone.

11. The assembly of claim 10, wherein the outside bottom surface comprises a substantially circular surface having four quadrants, wherein each quadrant of the outside bottom surface of the capacitive assembly comprises at least one of the capacitive plates.

12. The assembly of claim 10, wherein each capacitive plate and the bottom bore portion forms a capacitor.

13. The assembly of claim 10, wherein the capacitive assembly further comprises an integrated circuit having memory, wherein the integrated circuit is configured to:
store one or more measurements made by the capacitive assembly in the memory; and
transmit the one or more measurements to a reader when the reader is in proximity to the integrated circuit.

14. The assembly of claim 10, wherein the capacitive assembly further comprises an integrated circuit having memory, wherein the integrated circuit is configured to:
store a unique identifier associated with the set screw in the memory; and
transmit the unique identifier to a reader when the reader is in proximity to the integrated circuit.

15. The assembly of claim 10, wherein the capacitive assembly further comprises an integrated circuit having one or more of the following:
a radio frequency identification (RFID) chip; or
a near-field communication (NFC) chip.

16. The assembly of claim 10, wherein a gap exists between each of the capacitive plates and the bottom bore portion.

17. A spinal implant assembly comprising:
an anchoring member comprising a channel configured to receive a longitudinal member;
a set screw comprising a central opening that extends from a first end of the set screw toward a second end of the set screw, wherein the second end of the set screw comprises a bottom bore portion, wherein the set screw is configured to threadedly engage with the anchoring member, causing the longitudinal member to be captured in the channel; and
a capacitive assembly comprising:
an integrated circuit located within an internal portion of the capacitive assembly, and
a plurality of capacitive plates positioned on an outside bottom surface of the capacitive assembly, wherein each of the capacitive plates is in operable communication with the integrated circuit, wherein the capacitive assembly is configured to be received within the central opening of the set screw, such that the plurality of capacitive plates are positioned above the bottom bore portion.

18. The spinal implant assembly of claim 17, wherein the integrated circuit comprises memory, wherein the integrated circuit is configured to:
store one or more measurements made by the capacitive assembly in the memory; and
transmit the one or more measurements to a reader when the reader is in proximity to the integrated circuit.

19. The spinal implant assembly of claim 17, wherein the integrated circuit comprises memory, wherein the integrated circuit is configured to:
store a unique identifier associated with the set screw in the memory; and
transmit the unique identifier to a reader when the reader is in proximity to the integrated circuit.

20. The spinal implant assembly of claim 17, wherein the integrated circuit comprises one or more of the following:
A radio frequency identification (RFID) chip; or
a near-field communication (NFC) chip.

* * * * *